United States Patent [19]

Dessau

[11] Patent Number: 5,254,787
[45] Date of Patent: Oct. 19, 1993

[54] DEHYDROGENATION AND DEHYDROCYCLIZATION USING A NON-ACIDIC NU-87 CATALYST

[75] Inventor: Ralph M. Dessau, Edison, N.J.

[73] Assignee: Mobil Oil Corp., Fairfax, Va.

[21] Appl. No.: 941,811

[22] Filed: Sep. 8, 1992

[51] Int. Cl.$^5$ .................................... C07C 5/02
[52] U.S. Cl. .................... 585/654; 585/407; 585/418; 585/419; 585/420; 585/660
[58] Field of Search .............. 585/654, 407, 411, 419, 585/420

[56] References Cited

U.S. PATENT DOCUMENTS

| | | | |
|---|---|---|---|
| 4,347,394 | 8/1982 | Detz et al. | 585/419 |
| 4,652,360 | 3/1987 | Dessau | 208/138 |
| 4,699,708 | 10/1987 | Dessau | 208/111 |
| 4,868,145 | 9/1989 | Dessau et al. | 502/66 |
| 4,870,223 | 9/1989 | Ellig et al. | 585/419 |
| 4,990,710 | 2/1991 | Dessau et al. | 585/277 |
| 5,041,402 | 9/1991 | Casci et al. | 502/67 |
| 5,102,641 | 4/1992 | Casci et al. | 423/328 |

*Primary Examiner*—Asok Pal
*Assistant Examiner*—P. Achutamurthy
*Attorney, Agent, or Firm*—Alexander J. McKillop; Dennis P. Santini; Lori F. Cuomo

[57] ABSTRACT

A catalytic dehydrogenation and/or dehydrocyclization of paraffins. The aliphatic compound is contacted, under dehydrogenation conditions, with a Group VIA or Group VIII metal-containing non-acidic zeolite having the structure of NU-87 as the catalyst

14 Claims, No Drawings

DEHYDROGENATION AND DEHYDROCYCLIZATION USING A NON-ACIDIC NU-87 CATALYST

FIELD OF THE INVENTION

The invention relates to catalytic dehydrogenation and/or dehydrocyclization of paraffins. The catalytic dehydrogenation requires as the catalyst composition a non-acidic zeolite having the structure of NU-87 and a Group VIA or Group VIII metal. This catalyst composition can be employed as a reforming catalyst.

BACKGROUND OF THE INVENTION

Dehydrogenation of $C_2$–$C_5$ aliphatic compounds produces known compounds, the corresponding unsaturated analog. The products can be employed in various processes. The most likely use of the products produced by the invention is in conversion processes to produce a variety of petrochemicals or liquid fuels like poly gasoline, motor alkylate and methyl tertiary butyl ether. Alkanes containing at least 6 carbon atoms undergo dehydrogenation and cyclization to aromatic hydrocarbons, a process of dehydrocyclization, providing a gain in octane number.

Dehydrogenation requirements differ for each alkane. Those differing requirements reflect the reaction pathways involved and the thermodynamic properties of the starting materials and of the products. For example, butane dehydrogenation conditions can also effect butane isomerization and cracking, as major side reactions, which decrease the selectivity of the specific reaction for the product. When catalyzed by a solid catalyst, those cracking side-reactions can result in coking and/or aging of the catalyst necessitating regeneration procedures.

SUMMARY OF THE INVENTION

The present invention is directed to paraffin dehydrogenation and paraffin dehydrocyclization using a non-acidic catalyst composition. The composition comprises a Group VIA or VIII metal-containing non-acidic zeolite having the structure of NU-87. The non-acidic form of the zeolite combined with a dehydrogenation metal exhibit high selectivity for dehydrogenation and/or dehydrocyclization of paraffins.

DETAILED DESCRIPTION OF THE INVENTION

The catalyst for the catalytic dehydrogenation of the invention comprises a Group VIA or Group VIII metal and a non-acidic zeolite having the structure of NU-87. NU-87 is synthesized in accordance with U.S. Pat. No. 5,102,641, incorporated herein by reference. The cation(s) of zeolite NU-87 can be replaced by any cation of metals. Exchange may be carried out using a solution containing a salt of the appropriate cation.

The amount of Group VIA or Group VIII metal in the non-acidic catalyst composition employed can range from about 0.01 to about 30 weight percent and preferably 0.1 to about 10 weight percent? of the zeolite material. Platinum is the preferred Group VIA or Group VIII metal in the non-acidic catalyst composition.

Zeolites can be acidic or non-acidic, depending on the framework aluminum content and on the amount of compensating cations, such as $Na^+$, $K^+$, etc. The compositions comprising a Group VIA or Group VIII metal combined with the non-acidic zeolite having the structure of NU-87 do not exhibit any appreciable acid activity. These catalysts would meet the criteria of non-acidic catalysts described by Davis and Venuto, J. Catal. Vol. 15, p. 363 (1969). Thus, a non-equilibrium mixture of xylenes are formed from either n-octane or each individual methylheptane isomer, with the octane yielding more o-xylene and 2-methyl-heptane yielding mostly m-xylene, at conversions between and 10 and 60%. Alternatively, the non-acidic compositions will exhibit a pH of at least 6 when added to distilled deionized pH 7 water maintained under inert (such as argon) atmosphere; by an inert atmosphere in this context it means an atmosphere free of $CO_2$. Typically, in these tests, 100 mg of catalyst was added to 30 ml. of distilled deionized water. Some compositions will exhibit a pH of at least 7.5.

In materials of the invention, all cation-exchangeable sites are occupied by non-hydrogen (non-proton) and by non-hydrogen precursors, such as $NH_4^+$. Specifically, such sites are occupied by $Na^+$, $K^+$, $Cs^+$ or admixtures thereof. The alkali metals serve to neutralize any acidity due to framework aluminum. The source of alkali metal cation can derive from cations incorporated during synthesis, in excess of the aluminum content thereof. Conventional dealumination including steam treatment and aqueous acid treatment may be used to remove some of the aluminum from the NU-87 crystal framework. The final product may be treated with a basic solution of an alkali metal hydroxide as a final step prior to use, as described for example in U.S. Pat. No. 4,652,360, which is incorporated herein by reference. NU-87 containing preferably less than about 1.2 weight percent of aluminum is preferred.

In a preferred embodiment, the non-acidic Pt/NU-87 of the invention is prepared by treating with $Pt(NH_3)_4Cl_2$ in aqueous solution to incorporate the necessary platinum into the catalyst composition formulation followed by base treatment with an alkali metal hydroxide.

In a further embodiment, the Group VIA or VIII metal-containing zeolite having the structure of NU-87 can contain a modifier selected from the group consisting of tin, indium, thallium, lead, gallium and sulfur. The use of a modifier in a Group VIII metal containing non-acidic crystalline material is described in U.S. Pat. No. 4,990,710, incorporated herein by reference.

The modifier content of the zeolite can range from 0.01 to 20 weight percent. Practically, the modifier content will range from 0.1 to 10 weight percent.

The non-acidic dehydrogenation metal containing materials of the invention can be combined with a matrix or binder material to render them attrition resistant and more resistant to the severity of the conditions to which they will be exposed during use in hydrocarbon conversion applications. Such matrix materials include synthetic or natural substances as well as inorganic materials such as clay, silica and/or metal oxides, such as titania or zirconia. The latter may be either naturally occurring or in the form of gelatinous precipitates or gels including mixtures of silica and metal oxides. Naturally occurring clays which can be composited with the zeolite include those of the montmorillonite and kaolin families. These clays can be used in the raw state as originally mined or initially subjected to calcination, acid treatment or chemical modification. These materials, i.e., clays, oxides, etc., function, in part, as binders for the catalyst.

In addition to the foregoing materials, the zeolites may be composited with a porous matrix material, such as alumina, silica-alumina, silica-magnesia, silica-zirconia, silica-thoria, silica-beryllia, silica-titania as well as ternary compositions, such a silica-alumina-thoria, silica-alumina-zirconia, silica-alumina-magensia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite. When used in dehydrogenation and/or dehydrocyclization, the material of the invention will preferably be combined with non-acidic matrix or binder materials. A preferred matrix or binder material would be silica or titania.

In accordance with the invention catalytic dehydrogenation comprises contacting an aliphatic hydrocarbon, with the catalyst composition of the invention to produce the corresponding unsaturated analog together with hydrogen. The catalytic dehydrogenation exhibits high selectivity with respect to production of said unsaturated analog, with substantially little, if any, selectivity for hydrogenolysis (cracking) and with substantially little, if any, selectivity for isomerization.

In dehydrogenation the feedstocks comprise at least one unsubstituted or substituted straight or branched chain aliphatic compound in which the aliphatic moiety has two to five carbon atoms. In accordance with the invention, dehydrogenation of the aliphatic moiety occurs to yield the unsaturated analog. When the aliphatic moiety is substituted, the substituents can be aryls substituted or unsubstituted. The class of reactants includes alkanes of 2 to 5 carbon atoms including ethane, propane, butane, isobutane, pentane and 2 methylbutane. Dehydrogenation of those respective alkane reactants will yield ethylene, propylene, butene, isobutene, pentene and isopentene.

The class of reactants includes olefins of 2 to 5 carbon atoms such as ethylene, butene, pentene, and isopentene. Dehydrogenation of ethylene will produce acetylene; dehydrogenation of butene will produce butadiene and dehydrogenation of isopentene will produce isoprene.

The class of reactants employed in the dehydrogenation of the invention includes aromatic substituted aliphatics. Preferably, the aliphatic group of the aryl substituted aliphatic contains less than four carbon atoms and more preferably more than 1 carbon atom. The aromatic substituted aliphatic reactants embrace unsubstituted aromatic aliphatics and alkyl substituted aromatic aliphatics and, similarly, each of the alkyls of said alkyl substituted alkylaryls contains preferably less than 4 carbon atoms. By way of illustration reactants such as ethyl benzene, diethylbenzene, ethyl toluene, and cumene are representative of these compounds. On dehydrogenation in accordance with the invention, ethyl benzene will produce styrene; p-ethyl toluene will produce p-methylstyrene; cumene, isopropenylbenzene; and diethylbenzene, divinylbenzene.

In accordance with the invention, catalytic dehydrogenation conditions include pressures varying from subatmospheric, to atmospheric to greater than atmospheric. Preferred pressures range from 0.1 atmospheres to atmospheric. However, pressures up to 500 psig can be employed. The dehydrogenation is conducted at elevated temperatures ranging from 300° C. to 700° C. and most preferably from 400° C. to 600° C. Reactor inlet $H_2$/feed ratios are 5 or less; even at reactor inlet ratios of zero (0), there will be a hydrogen partial pressure in the reactor because hydrogen is a bi-product of dehydrogenation. The liquid hourly space velocity is 0.1 to 50, preferably 0.5 to 10.

Under these conditions, the catalytic dehydrogenation of the invention exhibits low selectivity for undesirable hydrogenolysis or isomerization.

Dehydrogenation may be conducted in the presence or absence of purposefully added hydrogen and in the presence of diluents inert to conditions of the catalytic dehydrogenation such as nitrogen and methane. In particular, dehydrogenation can be advantageously conducted at low hydrogen pressure.

Dehydrocyclization in accordance with the invention comprises contacting an aliphatic of at least six (6) carbon atoms with the catalytic composition comprising a dehydrogenation/hydrogenation metal which can be any Group VIA or VIII metal, preferably platinum.

The feedstocks charge to the new reforming process can be straightrun, thermal, or hydrocracker naphtha. Preferably, for high increases in the aromatic content and high octane numbers of the reformate, the charge to the reformer is a naphtha rich in $C_6$ and $C_7$ paraffins; these are generally difficult to reform selectively using conventional catalysts (such as chlorided Pt-alumina) Naphthas can be obtained by separating the charge into two fractions: a light naphtha and a heavy naphtha. Conventionally such separation is by distillation. The boiling range of the light naphtha is from about 80° F. to about 400° F. and the boiling range of the heavy naphtha will be from up to about 650° F. The light naphtha will be rich in $C_6$-$C_{10}$ paraffins, and specifically $C_6$ and $C_7$ paraffins. In accordance with one embodiment, when the light naphtha is reformed in accordance with the invention, the heavy naphtha will be processed by conventional reforming. The naphtha fractions may be hydrotreated prior to reforming; but hydrotreating is not necessarily required when using the catalyst in accordance with the invention, as the catalyst does not appear to be deactivated by, e.g., sulfur. Initial hydrotreating of a hydrocarbon feed serves to convert sulfur, nitrogen and oxygen derivatives of hydrocarbon to hydrogen sulfide, ammonia, and water while depositing metal contaminant from hydrodecomposition of any organo-metal compounds. Where desired, interstage processing of the effluent from the hydrotreating zone may be effected. Such interstage processing may be undertaken, for example, to provide additional hydrogen, to add or remove heat or to withdraw a portion of the hydrotreated stream for treatment which need not be reformed. Hydrotreating of the heavy naphtha fraction may be essential, prior to reforming in a conventional reforming process. Suitably, the temperature in the hydrotreating catalyst bed will be within the approximate range of 550° F. to 850° F. The feed is conducted through the bed at an overall space velocity between about 0.1 and about 10 and preferably between 0.2 and about 2, with hydrogen initially present in the hydrotreating zone in an amount between about 1000 and 10,000 standard cubic feet per barrel of feed, corresponding to a ratio of between about 2.4 and about 24 moles of hydrogen per mole of hydrocarbon. The catalyst may be any of the known hydrotreating catalysts, many of which are available as staple articles of commerce. These hydrotreating catalysts are generally metals or metal oxides of Group VIB and/or Group VIII deposited on a solid porous support, such as silica and/or metal oxides such as alumina, titania, zirconia, or mixtures thereof. Representative Group VIB metals include molybdenum, chromium and tungsten and Group VIII metals include nickel, cobalt, palladium and platinum. These metal components are deposited, in the form of metals or metal oxides, on the indicated supports in amounts generally between about 0.1 and about 20 weight percent. One particularly useful hydrotreating catalyst is a commercial catalyst known as Chevron ICR 106 which is a nickel-tungsten- alumina-silica-titania catalyst.

When dehydrogenation, dehydrocyclization or reforming is undertaken over the catalyst in accordance with the invention, the temperature can range broadly from 800° F. to 1100° F., generally being greater than about 900° F., preferably being 900° F. (482° C.) to 1050° F.; the pressure will be from about 1 atmosphere to 500 psig, preferably from 30 psig to 250 psig; inlet $H_2$/hydrocarbon can be 5 or less, even zero (0) (because of hydrogen production during reforming, there will be a hydrogen partial pressure in the unit); while the LHSV (liquid hourly space velocity) can be 0.1 to 20, preferably 0.1 to 10.

Reforming of the heavy naphtha fraction, boiling range of up to 650° F. can be undertaken separately from the light naphtha fraction, by conventional reforming. Conventional reforming may be semi-regenerative, cyclic or continuous. Process conditions in reforming include pressures of about 0 to 500 psig, preferably, the pressures used herein range from 0-250 psig and most preferably are 0-100 psig; temperatures of 800 to 1100° F.; $H_2$/HC molar ratios of 0 to 20:1 preferably of about 2:1 to about 6:1; LHSV of 0.1 to 20 $hr^{-1}$. Conventional reforming catalysts for this stage can include conventional reforming hydrogenation/dehydrogenation metals on aluminas. Those reforming hydrogenation/dehydrogenation metals include platinum; platinum-rhenium; platinum with iridium, rhenium, rhodium or admixtures thereof; or platinum/tin. These hydrogenation/dehydrogenation metal combinations are on alumina and are chlorided; generally they are presulfided prior to use on feeds containing less than about 1 ppm sulfur.

Selectivity and aging characteristics at low hydrogen partial pressures may be superior to conventional non-zeolitic reforming catalysts. With these catalysts, the reforming process can be run in the absence of added hydrogen, and preferably even, in the presence of diluents such as nitrogen, methane, propane, pentanes, and $C_6$-$C_8$ aromatics.

The non-acidic Group VIA or Group VIII metal-containing NU-87 of the invention used in catalysis results in a decrease in the hydrogen content of the reactant to produce a product having the same number of carbon atoms as the number of carbon atoms in the reactant.

The following examples illustrate the process of the present invention.

EXAMPLES

Example 1

This example illustrates the preparation of a non-acidic Pt/NU-87 catalyst. An as-synthesized NU-87 (Si/Al=32) was calcined first in nitrogen, then in air, to 540° C. Four grams of the calcined NU-87 was added to 125 ml water containing 50 mg Pt and stirred overnight at room temperature. The solid was filtered, washed and dried, and then calcined in air to 350° C. The calcined Pt/NU-87 was slurried in a 0.1M CsCl solution, with the pH maintained at 8.0 via continuous addition of dilute CsOH. After 8 hours, the solid was recovered, washed and dried. The non-acidic Pt/NU-87 product contained 0.52 wt % Pt, 5.34 wt % Cs, 1.10 wt % Al and 42.03 wt % Si.

Example 2

The non-acidic nature of the catalyst of Example 1 was confirmed by its ability to aromatize n-hexane to benzene in high yield. The ability of the non-acidic Pt/NU-87 to aromatize n-hexane to benzene was assessed at 500° C. and 150 torr n-hexane in hydrogen. Normal hexane was passed over 0.5 g of the catalyst of Example 1 at 12.5 cc/min. Conversion of n-hexane was 99.9%, with benzene produced in 75.6% yield.

Example 3

This example illustrates for comparison the preparation of a Pt/NU-87 catalyst not subjected to base treatment. An as-synthesized NU-87 (Si/Al=32) was calcined first in nitrogen, then in air, to 540° C. Then, 2.1 grams of the calcined NU-87 was added to 70 ml of water containing 26 mg Pt(NH and stirred overnight at room temperature. The solid was filtered, washed and dried, and then calcined in air to 350° C. Unlike the catalyst of Example 1, the catalyst of this example was not subjected to base exchange with CsOH. The acidic Pt/NU-87 contained 0.72 wt. % Pt, 0.58 wt. % Na, 1.20 wt. % Al, and 42.41 wt. % Si. The molar ratio of Na/Al is less than about 0.6, i.e., not enough Na to neutralize the Al sites responsible for acidity.

Example 4

The acidic nature of the catalyst of Example 3 was confirmed by its inability to aromatize n-hexane to benzene in high yields under the same process conditions as set forth in Example 2. Conversion of n-hexane was 99.9%, with benzene produced in less than 5% yield. The non-acidic Pt/NU-87 of Example 1 greatly increased the benzene yield (75.6% yield as compared to the Pt/NU-87 of Example 2.

Example 5

The ability of the non-acidic Pt/NU-87 of Example 1 to aromatize n-octane was assessed at 400° C. and 15 torr n-octane in hydrogen. Normal octane was passed over 0.5 g of the catalyst of Example I at 25 cc/min. Conversion of n-octane was 96.8%. The yield of aromatics included:

| | |
|---|---|
| benzene | 5.0% |
| toluene | 9.6% |
| ethylbenzene | 17.2% |
| p + m xylenes | 3.5% |
| ortho-xylene | 4.0% |

The $C_6$- products were 44.4%.

Example 6

Under similar conditions, isobutane was dehydrogenated. Isobutane was passed over 0.5 g of the catalyst of Example 1 at 550° C. and at a flow rate of 25 cc/min. A yield of 26.1% isobutene was obtained, together with 1.9% $C_3$- and 4.4% linear $C_4$'s.

Changes and modifications in the specifically described embodiments can be carried out without departing from the scope of the invention which is intended to be limited only by the scope of the appended claims.

What is claimed is:

1. A process for the dehydrogenation of an aliphatic compound containing at least 2 carbon atoms comprising contacting the aliphatic compound under dehydrogenation conditions with a catalyst composition comprising a non-acidic zeolite having the structure of NU-87 and a Group VIA or Group VIII metal.

2. The process of claim 1 wherein said aliphatic compound contains from 2 to 5 carbon atoms.

3. The process of claim 1, wherein said aliphatic compound is selected from the group consisting of ethane, propane, butane, isobutane, pentane, isopentane, or mixtures thereof.

4. The process of claim 3 wherein said aliphatic compound is isobutane.

5. The process of claim 1 wherein said aliphatic compound contains at least 6 carbon atoms.

6. The process of claim 1 wherein the dehydrogenation conditions include a temperature in the range of from about 300 to about 700° C.

7. The process of claim 1 wherein the Group VIII metal is platinum.

8. The process of claim 1 wherein said Group VIA or Group VIII metal is in an amount in the range of from about 0.01 to about 30 weight percent.

9. The process of claim 1 wherein said catalyst composition comprising a non-acidic zeolite having the structure of NU-87 and a Group VIA or Group VIII metal contains a modifier, wherein said modifier is selected from the group consisting of tin, indium, gallium, lead, thallium and sulfur.

10. The process of claim 9 wherein said modifier is in an amount in the range of from about 0.01 to about 20 weight percent of the catalyst composition.

11. A process for dehydrogenation of an aliphatic compound containing at least 6 carbon atoms which comprises contacting the aliphatic compound, under dehydrogenation conditions, with a catalyst composition comprising a non-acidic zeolite having the structure of NU-87 and a Group VIA or Group VIII metal, to convert said aliphatic compound to a product comprising aromatics.

12. The process of claim 11 wherein said VIII metal is platinum.

13. The process of claim 11 wherein said aliphatic compound containing at least 6 carbon atoms is hexane, heptane or octane.

14. A process for the aromatization of a naphtha feedstock containing $C_6-C_{10}$ paraffins comprising contacting said naphtha feedstock, under reforming conditions, with a catalyst composition comprising a non-acidic zeolite having the structure of NU-87 and a Group VIA or Group VIII metal.

* * * * *